(12) United States Patent
Krummen et al.

(10) Patent No.: US 10,067,100 B2
(45) Date of Patent: Sep. 4, 2018

(54) METHOD AND APPARATUS FOR PRECONCENTRATING A GASEOUS SAMPLE

(71) Applicant: Thermo Fisher Scientific (Bremen) GmbH, Bremen (DE)

(72) Inventors: Michael Krummen, Bad Zwischenahn (DE); Johannes Schwieters, Ganderkesee (DE); Hans-Juergen Schlueter, Bremen (DE); Oliver Kracht, Bremen (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 323 days.

(21) Appl. No.: 15/139,703

(22) Filed: Apr. 27, 2016

(65) Prior Publication Data

US 2016/0320355 A1    Nov. 3, 2016

(30) Foreign Application Priority Data

Apr. 30, 2015 (GB) .................................. 1507441.2

(51) Int. Cl.
*G01N 30/10* (2006.01)
*G01N 30/32* (2006.01)
*G01N 30/38* (2006.01)
*G01N 30/88* (2006.01)

(52) U.S. Cl.
CPC ............. *G01N 30/10* (2013.01); *G01N 30/32* (2013.01); *G01N 2030/324* (2013.01); *G01N 2030/383* (2013.01); *G01N 2030/8868* (2013.01); *G01N 2030/8886* (2013.01)

(58) Field of Classification Search
CPC ...................................................... G01N 3/10
See application file for complete search history.

(56) References Cited

U.S. PATENT DOCUMENTS

| | | |
|---|---|---|
| 4,872,334 A | 10/1989 | Watanabe |
| 6,649,129 B1 | 11/2003 | Neal |
| 2004/0035183 A1 | 2/2004 | O'Brien et al. |

*Primary Examiner* — Jyoti Nagpaul
(74) *Attorney, Agent, or Firm* — David A. Schell

(57) ABSTRACT

A system for concentrating an analyte gas in a gas stream of an analytical system is provided. The system comprises at least one separation device, at least one gas inlet line, at least one detector, at least one gas outlet line, a first split line in connected to the gas inlet line, and a first split valve for controlling gas flow in the first split line. Also provided is a method for concentrating an analyte gas.

32 Claims, 6 Drawing Sheets

METHOD AND APPARATUS FOR PRECONCENTRATING A GASEOUS SAMPLE

FIELD

The invention relates to a continuous gas stream system for concentrating samples in analytical instruments, such as elemental analyzers, gas chromatographs and mass spectrometers. The invention furthermore relates to a method for preconcentrating a sample for analysis in analytical instruments.

BACKGROUND

Elemental analysis is a method for the determination of carbon, nitrogen, hydrogen, oxygen and/or sulphur composition of different materials, including liquids, solids and gases. During elemental analysis, samples are typically converted to simple gases such as $H_2$, CO, $CO_2$, $N_2$, $SO_2$, and $H_2O$ by combustion in a high temperature furnace (usually at or above 1000° C.), usually with aid of catalysts to facilitate the combustion. The combustion products are carried by an inert carrier gas (He or Ar) to a detector. To allow quantitative or qualitative determination of each gas species, the mixture is separated in one or more chromatographic columns, such as a gas chromatographic column or by adsorption/thermodesorption techniques, and detected using for example thermal conductivity detection (TCD), UV fluorescence, optical absorption spectroscopy (UV, Visible or IR), flame photometric detection, atomic absorption spectroscopy, inductively coupled plasma optical emission spectrometry (ICP-OES), inductively coupled plasma mass spectrometry (ICP-MS), glow discharge mass spectrometry (GD-MS), or by mass spectrometers for isotope ratios.

Typical systems comprise a reactor to convert sample material to simple gases, one or more chemical traps to adsorb undesired gas analytes such as $H_2O$, one or more separation columns and a detector which can for example be a gas sensor and/or a mass spectrometer or one of the other detection systems mentioned above. The flushed volume of reactors and separation devices determines the required carrier gas flow in the system, i.e. the greater the flushed volume the higher is the required gas flow. The carrier gas flow is commonly in the range of 40-300 ml/min, but can be as low as a few mL/min up to 1000 mL/min.

The gaseous combustion products that are to be detected are transported through the system by a carrier gas, such as helium or argon. The carrier gas however dilutes the gas molecules that are generated during sample conversion. As a result, small gas amounts become difficult to detect accurately and precisely; in other words, the signal-to-noise ratio becomes unfavourable.

Concentrating the sample gas prior to detection represents one possible solution to this dilemma. Methods for preconcentrating samples are known in the art. For example, common preconcentrating methods use adsorption and desorption techniques, sometimes in conjunction with cryogenic traps. In general, the adsorption takes place on the surface of an adsorbent. High sample amounts load the traps until the amount of the trapped analyte is sufficient for a significant detector signal. The release of the analyte is commonly controlled by temperature ramps. The desorption time is much shorter than the adsorption time which eventually increases the analyte in the carrier gas flow.

By way of example, Hansen & Sommer (Rapid Commun. Mass Spectrom. 2007; 21: 314-318) describe use of an ashtray system for collecting residual gases, for subsequent detection in a mass spectrometer.

Other preconcentration techniques make use of membranes where the desired analyte gas passes through the membrane while the remaining gas mixture is denied. The carrier gas flow for the analyte can be reduced so to concentrate it. In methods described in U.S. Pat. No. 5,142,143A, the adsorbed gases are released into lower pressure with a low flow of carrier gas where the desorbed gas therefore has a greater density than the carrier gas.

U.S. Pat. No. 6,155,097A describes a system for increasing concentration of trace vapor in a carrier medium, air in this instance by passing it through a membrane gas separator. The gas separator preferentially passes a portion of the trace vapor and rejects all but a very small portion of the carrier medium. The sample, concentrated in trace vapor with respect to the carrier medium, is then compressed by a turbomolecular pump resulting in an increase in density of the trace vapor at the exhaust port of the pump.

Another system known in the art is described in U.S. Pat. No. 6,649,129, which discloses a system for concentrating a gas sample using a cryofocuser, for delivery to a gas chromatograph.

U.S. Pat. No. 4,872,334 discloses an apparatus and method for temperature programmed capillary column gas chromatography. The apparatus is characterized in that it has two flow paths for carrier gas which can join to one flow path before a sample injection device, and one of the flow paths has a valve which can rapidly stop or decrease the flow of the carrier gas in that flow path.

US 2014/0283580 discloses a system for analyzing rare gases, that is based on trapping by means of a getterizing substrate to achieve a superconcentrated rare gas that is subsequently extracted for analysis.

In WO 2011/070574, an apparatus is described that includes a chamber for concentrating at least one analyte in a gaseous sample. Following concentrating the analyte, a carrier gas is used to transfer the concentrated analyte into a chromatographic separator for analysis and subsequent detection.

All of these previously described systems suffer from the drawback of requiring additional devices for concentrating analyte gas, such as traps, membranes or sorbent materials.

The present invention has been made against this background, to provide a system and method for preconcentrating analytes which addresses one or more of the issues mentioned.

SUMMARY

The present invention provides a system that is capable of concentrating an analyte gas by reducing flow of carrier gas in a continuous flow system, without the use of membranes, traps or solvents, and by maintaining flow direction. The system is thus capable of increasing signal-to-noise of detection signals following during separation of analytes, without reducing the amount of analyte that is being analyzed.

In accordance with a first aspect of the invention, there is provided a system for concentrating an analyte gas in a gas stream of an analytical system, the system comprising: (i) at least one separation device, for separating components of an analyte gas; (ii) at least one gas inlet line, for delivering the analyte gas from a supply of analyte gas to the separation device; (iii) at least one detector, for detecting components of the analyte gas; (iv) at least one gas outlet line, for delivering the components from the separation device to the detector; and (v) a first split line in fluid communication with the gas inlet line at a first junction, and a first split valve for controlling gas flow in the first split line. In one preferred embodiment, the system further comprises a second split line in fluid communication with the gas outlet line at a second junction, upstream from the detector, and a second split valve for controlling gas flow in the second split line. In some embodiments, the system comprises one gas inlet line and one gas outlet line, for delivering analyte gas into and from the separation device. In some embodiments, multiple separation devices can be arranged in the system, wherein one or more further separation devices are arranged on the gas outlet line from the first separation device. The outlet of the last separation device preferably is connected to the detector.

The invention can also extend to such a system in, or in combination with, an elemental analyzer. The invention can further extend to such a system in, or in combination with, a mass spectrometer.

A further aspect of the invention relates to an elemental analyzer having a system for concentrating an analyte gas as described herein.

Another aspect of the invention provides a method of concentrating a sample gas for detection in a continuous flow retention-based analytical device having a gas inlet and a gas outlet, the method comprising steps of: (i) providing a stream of gas into the analytical device at a first flow rate, wherein the gas contains an analyte gas that is temporarily retained in the device and a carrier gas that is not retained; (ii) reducing the flow rate of the carrier gas into the analytical device to a second flow rate prior to the analyte gas emerging at the gas outlet of the analytical device, wherein the second flow rate is lower than the first flow rate. As a consequence of the reduction in flow rate into the analytical device the analyte gas is concentrated in the carrier gas as it travels through the retention-based analytical device at the second flow rate. The retention-based analytical device can be a chromatograph column, for example a gas chromatograph column.

The method preferably further comprises providing a first split line for the flow of gas upstream of the gas inlet and providing a second split line downstream of the outlet for the analyte and carrier gas; and further comprises having the first split line closed and the second split line open while the gas flows into the device at the first flow rate and having first split line open and the second split line closed while the carrier gas flows into the device at the second flow rate. The gas flows from the outlet of the device into a detector. The flow rate into the detector is preferably maintained at a constant or substantially constant flow rate.

In some embodiments the analyte gas comprises a plurality of components (e.g., $N_2$, $CO_2$ and $SO_2$) that are temporarily retained in the separation device; the method further comprising reducing the flow rate of the carrier gas into the analytical device to the second flow rate prior to at least one selected component of the analyte gas (e.g., $SO_2$) emerging at the gas outlet of the analytical device; whereby the at least one selected component of the analyte gas is concentrated in the carrier gas as it travels through the retention-based analytical device at the second flow rate. In some embodiments, reducing the flow rate of the carrier gas into the analytical device to the second flow rate after at least one non-selected component of the analyte gas has emerged at the gas outlet of the analytical device.

In some embodiments, the method of concentrating a sample gas relates to a method of concentrating a sample gas in a system as described herein.

An analytical system, in this context, is a system for generating, separating and/or detecting samples or components of samples. An analytical system can for example be a system for detecting one or more molecular components of a sample. The analytical sample can for example be from an elemental analyzer (e.g. furnace and associated downstream chromtograph), that can be used in combination with a mass spectrometer.

A separation device, in the present context, is a device for separating components of samples. Usually a separation device is a device that separates molecular components of a sample, i.e. the device separates one or more molecular species from other one or more molecular species within a sample of such species. The mechanism of separation may comprise adsorption or absorption or a combination of these with respect to a stationary phase. In some embodiments, the separation device is a gas chromatograph (GC). The GC may, for example, be a packed GC column or a capillary GC column. With a GC column, the separation mechanism may be substantially adsorption (e.g. as with a packed column) or substantially absorption (e.g. as with a capillary column). In some embodiments, the separation device is an adsorption column that is packed with a material that adsorbs the sample and then is heated to selectively desorb components of the sample.

An analyte gas, in the present context, is a gas that contains at least one component that is to be analyzed. An analyte gas can for example be a sample gas.

A gas line, in the present context, refers to any channel, tube, conduit, capillary or the like for transporting gas. It will be apparent to the skilled person that additional components can be arranged on the gas line, such as junctions, valves, flow restrictions, flow controllers, gauges and the like. These components can sometimes also be in fluid connection with the gas line.

In the present context, a split line is a gas line for diverting gas away from another gas line. The two gas lines, the split line and the gas line, meet at a junction where the two lines are in fluid communication.

The analyte gas can be, and typically is, provided in a carrier gas. The carrier gas can be a suitable inert gas, such as helium or argon. The analyte gas can be provided by a chemical reactor, for example a chemical reactor or chemical furnace of an elemental analyzer. The sample can also be provided by a chemical trap, a cryogenic or a headspace equilibration device.

In general the first split valve can be connected on, or in fluid coupling to, the first split line, to permit flow of gas away from the inlet gas line into the first split line, as a function of the state of the valve. Likewise, the second split valve can be connected on, or in fluid coupling to, the second split line, to permit flow of gas away from the outlet gas line into the second split line, as a function of the state of the valve. In one embodiment, the first and/or second split valve has a first position in which gas is able to flow through the split line, and a second position in which gas is prevented from flowing through the split line In some embodiments, the first split line or the second split line, or both the first and the second split line, is open to atmosphere. However, one or more of the split lines can also be arranged so as to be in fluid connection to other gas lines, for example gas lines for providing gas into the supply of analyte gas, such as a chemical reactor. In another configuration, one or both split lines are arranged to provide gas flow into a sample introduction system, such as a sample injector or a sample autoinjector. In yet other configurations, the split lines are connected to other gas systems that can utilize the gas flow that is split away from the gas inlet and/or gas outlet lines of the system.

The first split valve or the second split valve, or both the first or second split valve, can be arranged at, or in fluid communication with, respectively the first and/or the second junction. The position of the valves can determine the gas flow in the split lines. The position of the valves can also be arranged so as to determine the gas flow in the gas inlet and/or gas outlet lines. The first split valve for controlling gas flow can be arranged at the first junction, the valve having a first position in which gas is able to flow through the first split line and the gas inlet line towards the separating device (first split open position), and a second position in which gas is able to flow along the gas inlet line towards the separation device but is prevented from flowing through the first split line (first split closed position). Likewise, the second split valve for controlling gas flow can be arranged at the second junction, the valve having a first position in which gas is able to flow through the second split line and the gas outlet line towards the detector (second split open position), and a second position in which gas is able to flow along the gas outlet line towards the detector but is prevented from flowing along the second split line (second split closed position).

A switch of flow can thus be provided by the position of the first and second split valves. In one configuration, both the first and second split valves are closed, and gas flow is maintained through the gas inlet and the gas outlet lines. A switch of flow, to allow gas to flow through the split lines, can be provided by opening the first and/or the second split valves. In one configuration, the position of the first split valve is changed to allow gas flow through the first split line. In this configuration, the relative flow of gas through the gas inlet line and the first split line will be determined by the dimensions of the two gas lines. Likewise, the position of the second split valve can be changed to allow gas flow through the second split line.

In one embodiment, there is a first split line on the gas inlet line. The first split line can preferably be arranged upstream from the separation device. Opening the first split line will lead to reduced flow of gas into the separation device, due to some of the gas being released through the first split line. If the first split line is opened after an analyte has entered the separation device in a flow of carrier gas, the analyte will move through the separation device at a reduced flow rate, since a part of the carrier gas is released through the first split line. As a consequence, the analyte will be more concentrated when released from the separation device, and hence the signal-to-noise for detecting the analyte in the detector will be improved.

In another embodiment, there are two split lines, a first split line and a second split line. The second split line can preferably be arranged downstream from the separation device, between the separation device and the detector. It can be advantageous that the first split line and the second split line be structured so as to provide for essentially similar gas flow through the split lines at a fixed pressure. It can for example be preferable to have the first split line and the second split line of substantially similar dimensions. It is an advantage of this configuration that a constant flow of gas can be provided into the detector, through two different configurations of the first and second split lines. In one configuration, both split valves are closed, and the flow of gas into the detector is determined by gas flow in the gas inlet line. In another configuration, either the first split line or the second split line is kept open. Simultaneous switching of the position of the valves in the first and second split lines will ensure that the gas flow into the detector will be constant. It can be advantageous, therefore, that the first and/or second split valves be controlled so as to provide for substantially similar or the same gas flow rate into the detector both when the analyte gas is being concentrated and when it is not. For example, in a first setting, while the first split valve is arranged so that the first split line is closed, the second split line can be open through the open second split valve, and the gas flow into the detector is reduced by the amount of gas that is released through the second split line. The position of the second split valve can then be changed to prevent flow into the second split line (second split line closed). Simultaneously, the first split valve position is changed to allow gas flow through the first split line (first split open). Due to the two split lines allowing the same gas flow, the same flow of gas will be released through the first split line as the second split line. As a consequence, by simultaneously alternating the position of the first and second split valves, a constant flow of gas into the detector will be provided. However, in the first configuration (second split line open, first split line closed), there is a high flow of gas into the separation device, that can for example be a separation column. If, within this high gas flow into the separation device, a sample gas is provided into the device, and if a switch to the second configuration (first split line open, second split line closed) is performed before an analyte emerges into the gas outlet line, from the separation device, the analyte will move at a reduced flow rate through the separation device. As a consequence, the analyte will be more concentrated when it emerges from the separation device than what it was when it entered the device, whilst flow into the detector remains constant.

The gas that is released into the first and/or second split lines is excess gas for the purpose of the setting of the system, i.e. gas that is not required or not desirable for achieving the desired effects of the system. For example, the excess gas flow at the second split line can represent gas flow that is not desirable in the detector, so as to minimize baseline effects when a lower flow rate of gas into the analytical device is provided through the release of excess gas through the opening of the first split line. Excess gas can also be gas that otherwise would lead to very high signal and/or signal saturation at the detector, for example as a result of high sample loads.

A further advantage of having a constant gas flow at the detector is that there will be less baseline shift, compared with a scenario in which gas flow into the detector is reduced.

It can be preferable to include a chemical trap upstream of the separation device, on the gas inlet line. The chemical trap can for example be a trap for absorbing water in the carrier and/or analyte gas. One advantage of the system is that by reducing carrier flow through the open split lines, there will be reduced carrier flow gas in the system. As a consequence, there will be less load on the chemical trap, thus extending its lifetime.

The analyte gas can be any gas that is generated in an analytical system. The supply of analyte gas can therefore be any suitable analytical system that provides analytes for separation and detection. In some embodiments, the analyte gas is a gas that is generated in an elemental analysis reactor, such as a furnace or combustion chamber. Such gases or gas components include for example $N_2$, $CO_2$, $SO_2$, $CO$ and $H_2$. Analyte gas can also include $H_2O$, which in some configurations is not desirable and can therefore be removed by means of a chemical trap.

The switch from a high gas flow to a reduced gas flow into the separation device, by means of the first and second split lines, can be done at any convenient time during analysis. The switch can be done selectively, for example based on the appearance of particular analytes at the detector of the system. The switch can also be preprogrammed, based on the configuration of the system, such as its capacity or volume, and the carrier gas flow rate. As an example, in one configuration, $N_2$ and $CO_2$ gases can be allowed to leave a gas chromatograph column at a first (high) flow rate. After their detection by the detector, gas flow is reduced, by either of the aforementioned means, so as to allow analytes with a higher retention time, such as $SO_2$ to be concentrated on the column.

Analyte gases that are generated in elemental analyzers are transported in a carrier gas through the system. Elemental analysis systems require a fairly large flow of carrier gas, which can typically be about 100-200 mL/min. As carrier gases can be fairly expensive, it can be advantageous to be able to switch between two or more sources of carrier in the gas system of the invention. In one such arrangement, there is a secondary carrier gas inlet provided on the gas inlet line, between the analyte gas supply (e.g., an elemental analysis reactor) and the first split line. The secondary carrier gas inlet line can be fluidly connected to the gas inlet line at a carrier gas junction, between the analyte gas supply and the first split line. This secondary carrier gas inlet line can be used for delivering a second carrier gas into the gas inlet line. For example, analyte gas from the analyte gas supply can be delivered into the separation device by means of a first carrier gas. It can then be desirable to switch to a second source of a different carrier gas that is delivered through a secondary carrier gas inlet line, e.g. because the secondary gas has better properties for chromatography.

The secondary carrier gas inlet line can have a gas flow control means for controlling gas flow into the inlet gas line.

Flow control means can in general be provided by any flow controller or regulated valve. Flow control means can for example be a mass flow controller or proportional valve, a volume flow controller, or a switchable combination of fixed flow restrictions that allow flow to be adjusted in discreet steps. Such flow control means are described in e.g. U.S. Pat. No. 7,928,369 and WO 2007/112876. Flow control means can be manually or automatically operated. They can also comprise one or more automatic or manual pressure regulator that is combined with at least one flow restriction downstream of the pressure regulator. Flow control means can be an automatic, electronic or digital flow controller, for example as disclosed in WO 2007/112876. An example of flow control means is the ConFloIV™ from Thermo Scientific.

The gas flow control means on the secondary carrier gas inlet line can thus for example be provided as a valve. The valve can for example be a regulated valve or a proportional valve.

In one embodiment, there is a valve arranged at, or in fluid communication with, the carrier gas junction, wherein the valve has a first position in which gas is able to flow from the analyte gas supply through the gas inlet line towards the first junction and in which the secondary carrier gas is prevented from flowing into the gas inlet line, and a second position in which gas is prevented from flowing from the analyte gas supply through the gas inlet line towards the first junction and in which the secondary carrier gas is able to flow into the gas inlet line, towards the first junction. Thus, a switch from one carrier gas to another can be performed by changing the position of a single valve. In one position of the valve, carrier gas flows through the analyte gas supply, through the gas inlet line and into the separation device. At the same time the second carrier gas is prevented from flowing into the gas inlet line by the position of the valve. In a second position of the valve, the second carrier gas is able to flow into the gas inlet line and into the separation device, while the first carrier gas is now prevented from flowing through the gas inlet line and into the separation device. In one embodiment, gas that is prevented from flowing into the gas inlet line is vented to atmosphere. It is also possible to configure the system so that the gas that is prevented from flowing into the gas inlet line is recycled, for example by means of a fluid connection to other gas lines, for example gas lines for providing gas into the supply of analyte gas, such as a chemical reactor. In another configuration, the gas can be recycled to provide gas flow into a sample introduction system, such as a sample injector or a sample autoinjector.

There can also be an additional split line on the gas inlet line that can be useful when switching between carrier gas supplies. Thus, an analyte gas split line can be provided, that is arranged on the gas inlet line, between the analyte gas supply and the carrier gas junction. The analyte gas split line can be provided with a valve for directing gas flow through the analyte gas split line. The valve can be provided as a switch valve at the junction between the analyte gas split line and the gas inlet line. The valve can have a first position in which gas is able to flow through the analyte gas split line and in which gas is prevented from flowing through the gas inlet line downstream from the analyte gas split line, and a second position in which gas is prevented from flowing through the analyte gas split line but is able to flow through the gas inlet line. In this configuration, it can be preferable to have a valve at the carrier gas junction, or in fluid communication with the carrier gas junction, wherein the valve has a first position in which gas is able to flow from the analyte gas supply through the gas inlet line towards the first junction and in which the secondary carrier gas is prevented from flowing into the gas inlet line, and a second position in which gas is prevented from flowing from the analyte gas supply through the gas inlet line towards the first junction and in which the secondary carrier gas is able to flow into the gas inlet line, towards the first junction. By means of these two valves, a switch between two sources of carrier gas can be made. In one configuration, gas flows from the analyte gas supply through the gas inlet line, and into the separation device. A valve for controlling gas flow in the analyte gas split line can be closed to gas flow in the split line, thus providing for gas flow from the analyte gas supply and into the separation device. A valve on the carrier gas inlet line can however be closed to prevent flow of the secondary carrier gas into the carrier gas inlet line. Switching the position of the two valves leads to a switch of gas flow, such that the secondary carrier gas is now provided by the secondary gas supply, through the open valve on the carrier gas inlet line. The valve at the analyte gas split line can be open to gas flow in the analyte gas split line, but prevent flow of gas from the analyte gas supply into the gas inlet line towards the separation device. The gas that then flows through the analyte gas split line can be vented to air, or it can be recycled for other use. There can optionally also be provided a carrier gas supply, for supplying gas into the secondary gas supply line.

In certain configurations of the system, it can be useful to arrange a second separation device on the gas outlet line, downstream from the separation device. Such an arrangement can be useful for example when high gas loads are being analyzed, and/or when an improved peak shape is required, so as to optimize separation. In some configurations, the second separation device is identical to the first separation device. In other configurations, the second separation device is different from the first separation device. The second separation device can for example comprise a second gas chromatograph column that can be largely identical to a first chromatograph column. The second separation device can also comprise a gas chromatograph column that is materially different from the first chromatograph column. In some embodiments, the second separation device is provided downstream from the second split line, between the second split line and the detector.

In some embodiments, the first split line and the second split line meet at a split line junction, from which there can be a third gas line, such as a flow control gas line. Thus, the two split lines can meet at a three-way junction with a gas line for regulating flow in the two split lines. In one embodiment, the split line junction comprises a split line valve for selectively controlling gas flow in the first split line, the second split line and/or the flow control gas line.

The split valve can have a first position, in which gas is able to flow through the first split line and into the flow control gas line, but is prevented from flowing through the second split line, and a second position in which gas is able to flow through the second split line and into the flow control gas line but is prevented from flowing through the first split line. In other words, the split valve can selectively regulate gas flow in the first split line and the second split line. The split valve can be a switch valve that in one position allows flow through the first split line and into the flow control gas line, and in a second position allows flow through the second split line and into the flow control gas line. In either configuration, the switch valve will prevent gas flow through the other split line and into the flow control gas line.

The flow control gas line can further include a flow controlling device. It will be appreciated that the flow controlling device can be any suitable device for controlling gas flow, such as a mass flow controller or proportional valve, a volume flow controller, or a switchable combination of fixed flow restrictions that allow flow to be adjusted in discrete steps.

The flow controlling device can preferably be provided as a switchable combination of fixed flow restrictions. In one embodiment, the flow controlling device is provided as a first restriction line and a second restriction line that meet at a restriction junction that is fluidly connected to the flow control gas line, and wherein the first restriction line and the second restriction line each comprise a fixed flow restriction for controlling gas flow.

There can be further provided a valve for controlling gas flow at the restriction junction. The valve can for example be a switch valve. In one embodiment, the valve has a first position, in which gas is able to flow through the first restriction line but is prevented from flowing through the second restriction line, and a second position, in which gas is able to flow through the second restriction line but is prevented from flowing through the first restriction line.

It will be appreciated that in this configuration of the system according to the invention, the first split valve and the second split valve may not be needed, because the split line valve is used to regulate flow in the first and second split lines. Thus, in some configurations, the split line valve is arranged on a system that does not have the first and/or second split line valves. Accordingly, the first split valve and the second split valve can be omitted from the system with this arrangement.

The arrangement and/or construction of the split lines according to the invention can be provided to achieve any desirable change in flow rate in the gas inlet and/or gas outlet lines when gas is vented through the split lines. For example, the split lines can be structured so that the ratio of flow through the split line to the flow through the gas inlet and/or gas outlet line is in the range of 2:1 to 20:1. In a preferred embodiment, the ratio of flow through the split line to the flow through the gas inlet and/or gas outlet line is in the range of 2:1 to 10:1. In another preferred embodiment, the ratio of flow through the split line to the flow through the gas inlet and/or gas outlet line is in the range of 2:1 to 5:1, 2:1 to 4:1, or 2:1 to 3:1.

Flow rates in the gas inlet lines and/or the gas outlet line according to the invention can be in the range of 10 to 1000 mL/min. In some preferred embodiments, the flow rate in the gas inlet line is in the range of 20 to 800 mL/min, in the range of 30 to 600 mL/min, in the range of 40 to 400 mL/min, in the range of 50 to 200 mL/min, or in the range of 60 to 100 mL/min. In some embodiments, the flow rate is about 60 mL/min, about 70 mL/min, about 80 mL/min, about 90 mL/min or about 100 mL/min. A higher flow rate according to the method of the invention, i.e. the flow rate with the split lines for reducing flow rate closed, can be in the above range. A lower flow rate in the gas inlet line, downstream from the first split line and/or in the gas outlet line, downstream from the second split line, can be in the range of 5 to 700 mL/min, such as in the range of 10 to 500 mL/min, in the range of 20 to 400 mL/min, in the range of 30 to 300 mL/min, in the range of 40 to 200 mL/min, in the range of 50 to 150 mL/min, or in the range of 50 to 100 mL/min.

As will be appreciated by the skilled person, the effect of preconcentrating analyte samples according to the invention is an improved signal to noise for detecting analytes. This is due to the fact that $c=n/V$, where c is concentration, n is the number of analyte molecules (or molar quantity of analyte), and V is the volume. By reducing the volume, the concentration of the analyte is increased. The split lines according to the invention can in some embodiments be open to air. In some embodiments, at least one of the split lines is connected to further gas lines, for example gas lines for recycling gas in the system and/or to sample delivery devices such as autosamplers.

The system according to the invention can be configured to include at least one controller for controlling valve position of at least one valve. The controller can preferably be adapted so that it can receive an input about at least one parameter that reflects the presence and/or absence, concentration, or pressure of gas in the system, and provide a signal to at least one valve based on the parameter information. In some embodiments, the controller is adapted to receive an input about the concentration about at least one analyte gas or component of analyte gas, and wherein the controller is able to adjust the position of at least one of the valves in the system based on the at least one measuring cell parameter. In some configurations, the controller is adapted to adjust the position of the first split valve, the second split valve and/or the split line valve where present. The valves can therefore also be adapted to be able to receive input from a controller, to change their position depending on the signal from the controller.

The controller can receive an input about the concentration and/or the presence or absence of at least one analyte gas or component of analyte gas in the gas outlet line, for example at the detector. Determination of the quantity of at least one gas is used to make a decision about the position of at least one valve in the system. For example, consider an embodiment of the invention that includes only a first split line. The controller can receive information from the detector about the presence of an analyte such as $N_2$ and/or $CO_2$ from a combustion reactor that typically elute first in a separation device such as a gas chromatograph column. The controller subsequently can send a signal to the first split line valve, which alters its position so as to allow gas flow into the first split line. This leads to a reduced gas flow into the column, and as a consequence, any subsequently eluting analytes on the column which have expected low concentrations, such as $SO_2$, will elute in a higher concentration than their concentration when entering the column, leading to an improved signal-to-noise for their detection.

The controller can in another embodiment be configured to control the valve position of the split line valve, so as to regulate gas flow in the first and second split lines. For example, the split line valve can be provided as a switch valve. In a first position, gas flows through the second split line and into the flow control gas line. Following a signal from the detector, the controller sends a signal to the split line valve, which changes position so as to prevent flow in the second split line, while opening the first split line for flow into the flow control gas line. In this manner, gas flow rate into the separation device is reduced, while the gas flow rate at the detector is essentially constant.

In certain embodiments, analyte gas supply in the system according to the invention is an elemental analyser. The analyser can be provided with a carrier gas supply that is used for transporting the analytes that are generated in the chemical reactor of the elemental analyser into the gas inlet line. Moreover, the system can include more than one supply of the carrier gas.

In certain embodiments of the invention, one or more of the junctions on the gas lines, such as the first junction, the second junction, the carrier gas junction, the split line junction and/or the restriction junction, are provided as a T-junction. In this context, a T-junction means any junction of three flow channels, i.e. a junction that contains three arms. The T-junction can be provided as a T-piece, as a Y-piece, or as a junction of three orthogonal channels. The junction can further be provided as a two-dimensional junction, wherein the three channels lie within the same plane, or the junction can be provided as a three dimensional structure, in which the three channels do not all lie in the same plane (i.e., as a three-dimensional "tripod").

Components of the system according to the invention, for example the gas inlet line, the gas outlet line, the split lines and the flow restriction lines, and including gas line junctions that are described herein, can be provided in a machined block, i.e. as one mechanical piece. This means that manufacturing of the system can be performed by machining out of a bulk of material, such as a metal block. Further, using T-junctions, with or without manufacturing in a machined block, ensures that flow through the openings in the junction are under full mechanical control. The T-junction design ensures that diffusion paths are well separated, which facilitates setup and calibration of the system, because its flow properties are well determined and predictable.

Further, it should be appreciated that the invention can be combined with gas inlet systems that are known in the art, including for example carrier gas inlet systems that provide gas flow for transporting analyte gas through the analyte gas supply and the gas inlet and outlet lines of the system. Such gas inlet systems will typically be provided so as to provide gas into the analyte gas supply, which is subsequently directed into the gas inlet line according to the invention.

The system according to the invention can be provided in combination with, or include, any suitable detector for detecting gaseous analytes. In some embodiments, the detector is a thermal conductivity detector (TCD). The detector can alternatively or also be a mass spectrometer, or any other suitable type of detector for gaseous analytes. In some embodiments, the system can include a thermal conductivity detector in combination with a mass spectrometer.

The above features along with additional details of the invention, are described further in the examples below.

BRIEF DESCRIPTION OF THE DRAWINGS

The skilled person will understand that the drawings, described below, are for illustration purposes only. The drawings are not intended to limit the scope of the present teachings in any way.

DESCRIPTION OF VARIOUS EMBODIMENTS

In the following, exemplary embodiments of the invention will be described, referring to the figures. These examples are provided to provide further understanding of the invention, without limiting its scope.

In the following description, series of steps are described. The skilled person will appreciate that unless required by the context, the order of steps is not critical for the resulting configuration and its effect. Further, it will be apparent to the skilled person that irrespective of the order of steps, the presence or absence of time delay between steps, can be present between some or all of the described steps.

It should be appreciated that the invention is applicable for regulating gas flow so as to concentrate analyte gas, and can be useful in various analytical systems. Further, the system and method according to the invention is illustrated in the embodiments that follow with a preferred embodiment of an elemental analyzer, but it should be appreciated that the invention is also applicable to other analytical systems for gas analysis. Accordingly, therefore, the gas that is being analyzed in the system will be variable.

Figure 1:
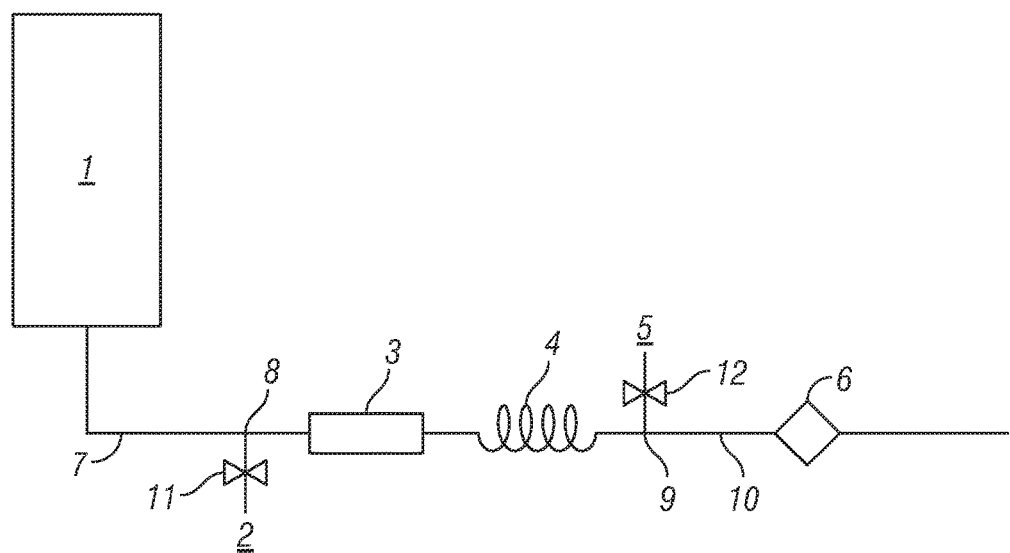
FIG. 1 shows schematic layout of an elemental analysis system that includes a system for concentrating gas according to an embodiment of the invention.

Referring to FIG. 1, there is schematically shown a chemical reactor 1 that is interfaced with a gas system according to the invention. The system has a gas inlet line 7, for providing analyte gas flow from the reactor and into gas chromatograph column 4. There is arranged a chemical trap 3 on the gas inlet line, for removing residual water from the analyte gas that passes through the gas inlet line. A gas outlet line 10 is provided for directing gas from the column 4 towards the detector 6.

A first split line 2 is provided, upstream from the column and the chemical trap, and a first split valve 11 on the first split line. A second split line 5 is provided on the gas outlet line, between the column and the detector, and on which a second split valve 12 is provided. The first split line meets the gas inlet line at a first junction 8, while the second split line meets the gas outlet line at a second junction 9. Although the split valves are shown to be located on the first and second split lines, respectively, it will be appreciated that the first and second split valves can be provided at the first and second junction, respectively. In general, it is preferred to have as few valves as possible along the gas inlet and gas outlet lines. Accordingly, it is preferable to arrange split valves between a split junction and the split opening If the first split valve and the second split valves are both closed, and/or both are positioned such that gas flow is provided through the gas inlet line and the gas outlet line but gas flow is prevented through the first and second split lines, there will be a gas flow from the chemical reactor at a flow rate that is provided by gas flow rate out of the reactor into the gas inlet line. As an example this flow rate may be 80 mL/min. To provide a constant baseline signal at the detector 6, the first split valve 11 is closed, so that gas does not flow into the first split line 2, prior to providing analyte gas into the system. In this arrangement, there is a flow of gas at a first, relatively high, flow rate in the gas inlet line and into the gas outlet line. In this example, the first flow rate will be 80 mL/min. A part of the gas stream (the excess gas) is released through the second split line 5, as the second split valve 12 is open, to provide a second, relatively low, flow rate of gas into the detector. As an example, the second flow rate may be 30 mL/min (i.e. with 50 mL split away). Subsequently, analyte gas is provided into the system at the first flow rate. The analyte gas will enter the separation device at the first flow rate. Following the entry of the analyte gas, which is provided in a stream of carrier gas, into the column 4, and prior to the appearance of the analyte that is desirable to concentrate in the gas outlet line, the first split line 2 is opened by changing the position of the first split valve 11 so as to allow gas flow through the first split line. In this way, the gas flows into the column 4 at the second, lower, flow rate. In this example, this is the flow rate of 30 mL/min (i.e. with 50 mL split away through the first split line). Simultaneously, the position of the second split valve 12 is changed, so as to prevent flow of gas through the second split line and the second flow rate (30 mL/min) is maintained into the detector. The restriction of the first split line should be the same as the sum of the restrictions of the second split line and the GC Column. The restrictions in the two split lines will therefore be adjusted so that the resulting flow thorugh the detector remains constant. The separation column will add an additional restriction to the system behind the first split valve. However, often, the restriction of the gas chromatography column is so small that it can be neglected. In such scenarios, the two split lines are of substantially equal dimensions, thus allowing for essentially identical gas flow at any given pressure. In other embodiments, the restrictions in the two split lines will be different, to account for the restriction in the gas chromatography column. As a consequence, during and after the simultaneous change of gas flow through the first and second split lines, the gas flow into the detector will be maintained at the second flow rate. However, gas flow into the column is now lower at the second flow rate, which results in a concentration of the remaining desired analyte gas on the column. When the analyte gas exits the column, it will do so at the second flow rate, resulting in an increased signal-to-noise of the detection of the analyte. In this example, there is a concentration of the analyte by a factor 2.66.

The switching of position of the first and second split valves is preferably controlled by a controller (not shown). The controller can be configured to send a signal to change the position of the valves based on preset parameters, such as time, concentration or absence or presence of certain gases at the detector 6. For example, an analyte gas that is generated by a chemical reactor, especially a combustion reactor, can contain a mixture of gases, including $N_2$, $CO_2$, $H_2O$ and $SO_2$. In general, N and C are much more abundant than S in sample compounds. As a consequence, there will be a much lower concentration of $SO_2$ that is generated by combustion and reduction in an elemental analysis reactor than $N_2$ and $CO_2$. The analyte gas that exits the chemical reactor contains a mixture of $N_2$, $CO_2$, $H_2O$ and $SO_2$. Water is removed by the chemical trap 3, while $N_2$, $CO_2$ and $SO_2$ enter the separation column at essentially the same time, at the first flow rate. However, $N_2$ and $CO_2$ leave the separation column first. An excess portion of these gases are split away through the open second split line. Once these gases are detected by the detector, the controller is set to signal to the valves so that there is a simultaneous switch of position of the first and second split valves. As a consequence, $SO_2$ gas moves through the column at the second flow rate, and will appear at the detector in its entirety (due to the second split line being closed) and more concentrated than when entering the column.

Figure 2:
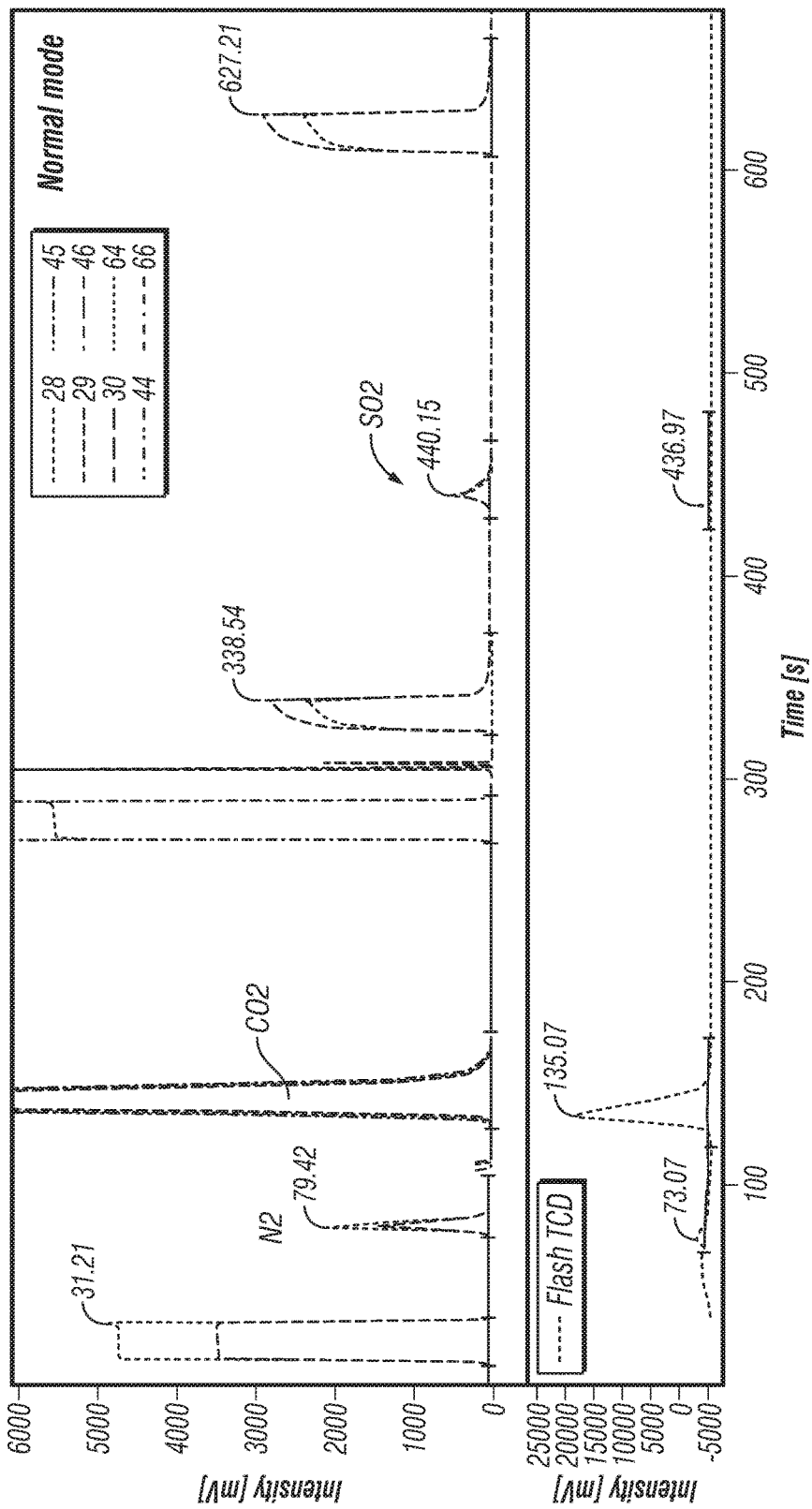
FIG. 2 shows a chromatograph that exemplifies the effect of preconcentration.
Figure 2:
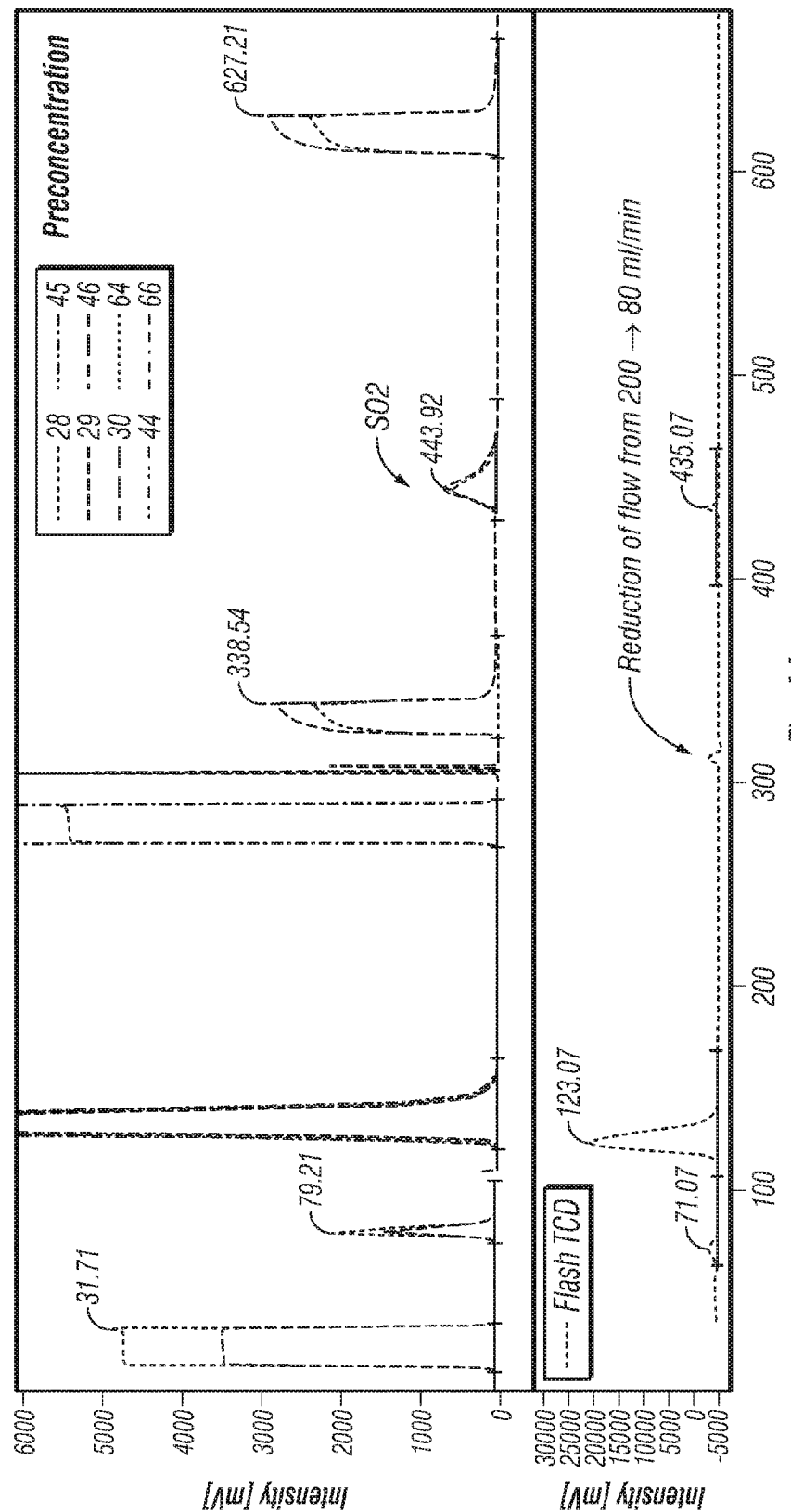

Turning to FIG. 2, an example of the preconcentration effect is illustrated. Shown are two chromatograms, that represent analysis without (upper chromatogram) and with (lower chromatogram) preconcentration of sample gas. In both chromatograms, results from analysis of about 1.05 mg of peat soil are shown. A sample gas containing a mixture of $N_2$, $CO_2$ and $SO_2$ is provided at a first flow rate of 200 mL/min. In a normal mode, i.e. with no change of flow rate, the amount of analyte gas that appears at the detector is as shown in the upper chromatogram. The amount of $SO_2$ in the sample is low compared with that of $N_2$ and $CO_2$, leading to relatively poor signal-to-noise. The effect of preconcentration is shown in the lower chromatogram. Here, a reduction of flow rate in the column from 200 mL/min to 80 mL/min results in a substantially increased peak height (⅔ increased intensity) and peak area (about 3-fold increased area), as a consequence of the flow of $SO_2$ at the lower flow rate, and without loss of $SO_2$ through the split line. As can be further appreciated, $SO_2$ is well separated from the other gases on the column.

Figure 3:
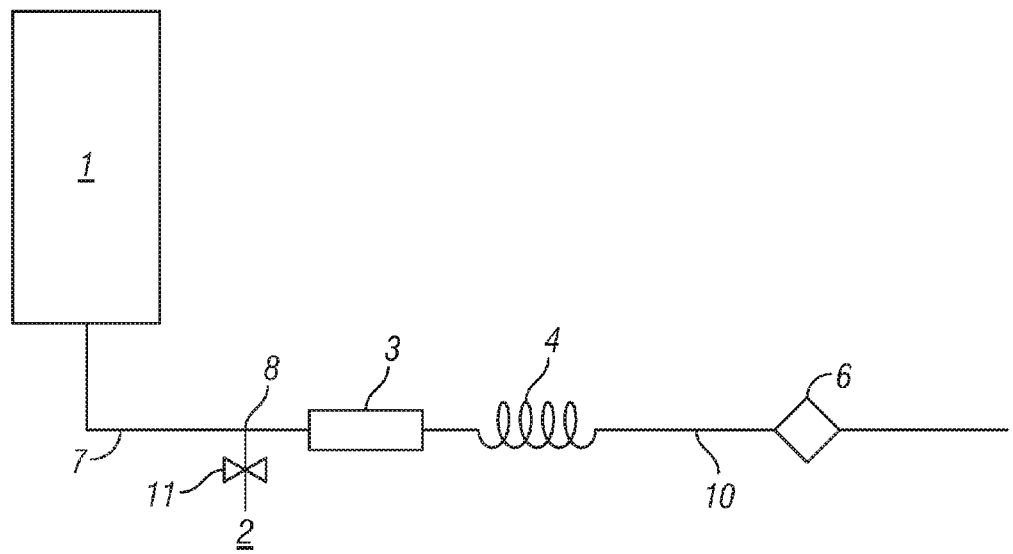
FIG. 3 shows a second embodiment, in which only a first split line is provided.

Turning to FIG. 3, an alternative embodiment is shown, that contains a single split line 2 that is arranged upstream from the column and the chemical trap. By opening the split line, the flow of gas in the separation column will be reduced. Thus, sample gases such as $N_2$ and/or $CO_2$ can be allowed to enter the column at a first flow rate, and the flow rate subsequently reduced by opening the valve 11 on the split line 2. It should be appreciated that since there is no second split line, there will be a concomitant decrease of gas flow at the detector 6. Thus, although this embodiment represents a simplified arrangement, there can be a baseline shift at the detector when the gas flow rate is reduced.

In some embodiments, high loads of analyte gas can be split away via split line 2 before the separation column 4 so to avoid column overload effects. If an $H_2O$ trap 3 is used, the reduced gas load extends the trapping capacity. For this type of analysis the carrier gas flow is commonly increased to 140-300 mL/min.

Figure 4:
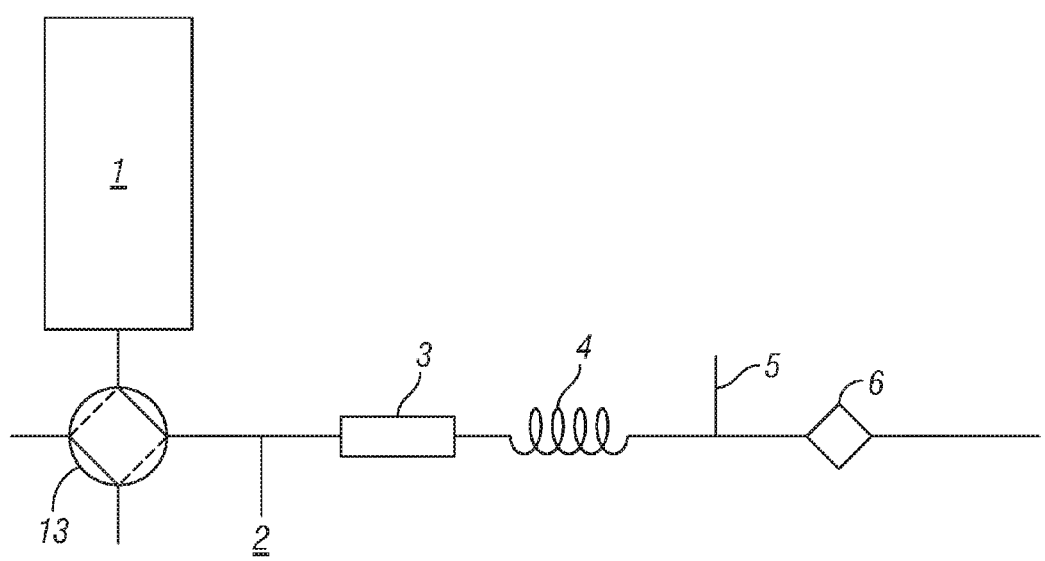
FIG. 4 shows a third embodiment, in which the system includes a first and second split lines, and further includes a four-way valve for providing a second carrier gas.

In FIG. 4, a 4-way valve 13 is arranged on the gas inlet line, downstream from the reactor 1 and upstream from the first split line 2. The valve is connected to a supply of secondary carrier gas (not shown), and also contains a line that is open to atmosphere. By means of this valve, the carrier gas in the system can be changed. Thus, in a first position, the valve is in the position indicated by the solid lines. In this position, analyte gas from the reactor is able to pass through the valve and into the separation column. At the same time, any flow of the secondary carrier gas will be vented to air. There can be arranged a large restriction at this vent, so that the consumption of the second carrier gas, when vented to air, is very low. The second split line 5 can be open during loading of the sample onto the column, to reduce sample amount at the detector. Following loading of the separation column, the position of the valve 13 can be changed, so that gas flow is along the dotted lines. In this configuration, gas from the reactor is vented to air, while the valve directs flow of secondary carrier gas into the separation column. An advantage of this configuration is the possibility to change carrier gas during chromatography, and also to reduce the amount required of the second carrier gas. The second carrier gas can for example be helium, which is more expensive than other carrier gas types, such as argon, but is advantageous for chromatographic resolution. Therefore, it can be advantageous to provide the high flow gas through the reactor in argon as carrier gas, and switch the carrier gas on the column to helium.

Figure 5:
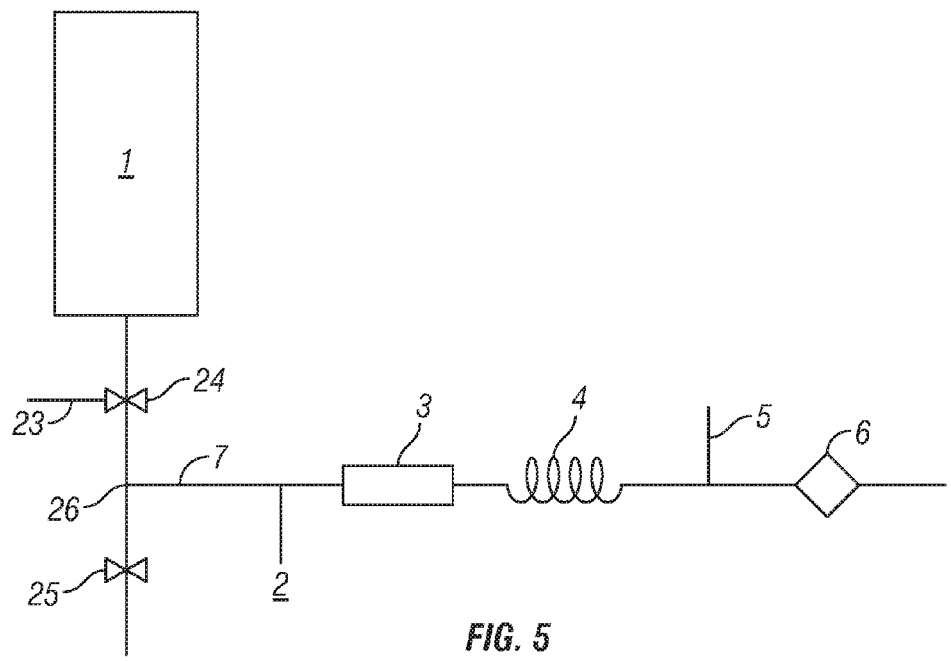
FIG. 5 shows another embodiment, wherein a second carrier gas is provided and that includes an additional split for venting gas from the reactor.

FIG. 5 shows an alternative arrangement, in which the four-way valve is replaced by two valves and an additional split line. Thus, a carrier gas supply (not shown) provides a source of a secondary carrier gas into the gas inlet line 7. Flow of the secondary carrier gas is regulated by a valve 25. The valve is shown as being arranged on a line from the secondary carrier gas supply to the carrier gas junction 26. Alternatively, the valve can be provided as a switch valve at the carrier gas junction. Furthermore, there is provided an additional analyte gas split line 23 downstream from the reactor 1. A switch valve 24 is provided at the junction between the gas inlet line 7 and the analyte gas split line 23. In a normal operation, gas flows from the reactor 1, through the gas inlet line 7 towards the first split 2. At this time, valves 24 and 25 are both closed, so as to prevent flow of secondary gas into the gas inlet line and venting of analyte gas through the analyte gas split line 23. By changing the position of switch valve 24, analyte gas from the reactor 1 is vented to atmosphere. Simultaneously, valve 25 can be opened to allow flow of the secondary carrier gas into the gas inlet line. An additional flow controller (not shown) can be arranged on the gas line that provides secondary carrier gas. Thus, in this alternative arrangement, a switch of carrier gas in the separation column and detector of the system can be performed, and gas flowing through the reactor will be vented to air. As will also be appreciated by the skilled person, alternative configurations and combinations of valves and split lines can be arranged to emulate the function of a 4-way valve.

Turning to FIG. 5, an embodiment is shown in which there are two separation columns 4 and 14. In this case, the first separation column 4 pre-separates the components of analyte gas. The second column is arranged downstream from the second split line. Gas flow through the first column can be adjusted by means of the first and second split lines as described in the above. Thus, the second split line can be kept open during sample load to split off excess amounts of $N_2$ and $CO_2$. After these gases have passed the second split line, the line is closed, while the first split line is simultaneously opened, to reduce flow rate in the first separation column. The second separation column will however operate continuously at the lower second flow rate. This configuration can be useful for example when there is a high sample load at the first separation column. Splitting away a part of the gas flow through the second split line will lead to a lesser sample load at the second column, resulting in improved separation and peak shape. The second separation column 14 can be selected for low flow rates so as to improve the peak shape.

Figure 6:
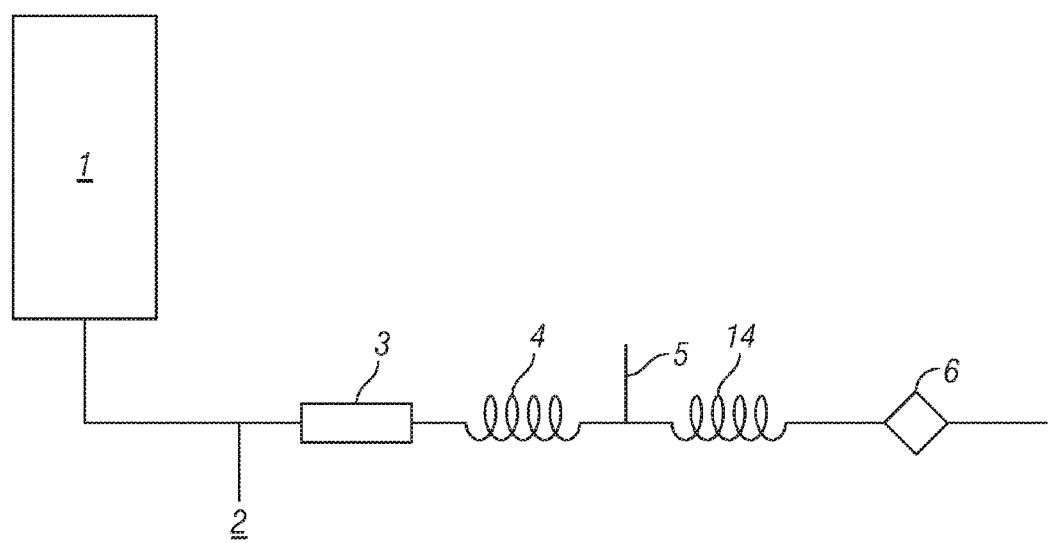
FIG. 6 shows a fifth embodiment, in which the system includes two separation devices.
Figure 7:
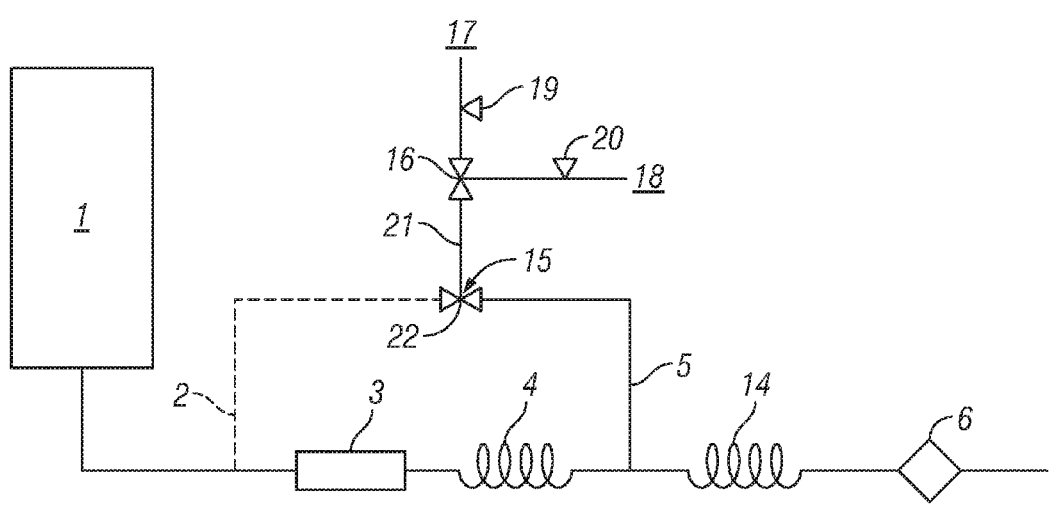
FIG. 7 shows a sixth embodiment, in which the first and second split lines merge, and in which flow rate in the first and second split lines is regulated by fixed flow restrictions that are arranged on separate restriction lines.

In FIG. 6, a further variant of the invention is illustrated. Here, a means for controlling gas flow in the split lines is provided by fixed flow restrictions, and the switch between restrictions is provided by switch valves. Thus, turning to FIG. 6, the split lines 2 (dotted lines) and 5 (solid lines) meet at a split line junction 15. A switch valve 22 is arranged at the junction, for selectively controlling gas flow in the first and second split lines. The switch valve is further connected to a flow control gas line 21. A second split valve 16 is arranged on the flow control gas line, for selectively directing gas flow into a first restriction line 18 or a second restriction line 17. Flow in the first and second restriction lines is controlled by means of a first flow restriction 20 and a second flow restriction 19, respectively. By means of the two switch valves, the flow in the first and/or second split lines can selectively be directed into the first or second restriction line, thus providing for the possibility to selectively controlling gas flow in each split line. The first switch valve 22 selectively opens flow in the first or second split lines, while the second switch valve 16 selectively opens to either of the two restriction lines, for selectively controlling flow in the split lines. This is useful if the total restriction requirement changes due to changes in the system conditions.

The skilled person will appreciate that further restriction lines can be suitably arranged so as to provide additional control of gas flow in the first and second split lines.

As an illustration of the advantage of this embodiment, the second separation column can be heated. Due to effects of heating, there will be an increased restriction on the column, leading to reduced gas flow. This can be balanced by switching to an increased restriction on the restriction line, by altering the position of the switch valve 16.

As should be appreciated based on the foregoing description of the invention, the invention provides a simple and low-cost solution to concentrate analyte gases in continuous flow systems, without the requirement of traps or other means for adsorbing and desorbing analytes. Further, the invention provides a means to reduce the amount of gas that is used during analysis, which will reduce risk of column overloading, and will also lead to improved lifetimes of chemical traps that are used for the adsorption of water in gas lines. The amount of sample that is released through the split lines, i.e. the so-called split ratio, can be adjusted based on the need of any given analysis. The separation column can also be selected according to the needs of any particular analysis, such as the type and flow of carrier gas and the nature of the analytes to be separated. Additionally, by arranging switch valves at the vent end of the split lines, the flow of gas in the split lines can be regulated in an automated manner. Additional restrictions can optionally be included, to provide further flow control opportunities.

As used herein, including in the claims, singular forms of terms are to be construed as also including the plural form and vice versa, unless the context indicates otherwise. Thus, it should be noted that as used herein, the singular forms "a," "an," and "the" include plural references unless the context clearly dictates otherwise.

Throughout the description and claims, the terms "comprise", "including", "having", and "contain" and their variations should be understood as meaning "including but not limited to", and are not intended to exclude other components.

It will be appreciated that variations to the foregoing embodiments of the invention can be made while still falling with the scope of the invention. Features disclosed in the specification, unless stated otherwise, can be replaced by alternative features serving the same, equivalent or similar purpose. Thus, unless stated otherwise, each feature disclosed represents one example of a generic series of equivalent or similar features.

Use of exemplary language, such as "for instance", "such as", "for example" and the like, is merely intended to better illustrate the invention and does not indicate a limitation on the scope of the invention unless so claimed. Any steps described in the specification may be performed in any order or simultaneously, unless the context clearly indicates otherwise.

All of the features and/or steps disclosed in the specification can be combined in any combination, except for combinations where at least some of the features and/or steps are mutually exclusive. In particular, preferred features of the invention are applicable to all aspects of the invention and may be used in any combination.

The invention claimed is:

1. A system for concentrating an analyte gas in a gas stream of an analytical system, the system comprising
at least one separation device, for separating components of an analyte gas;
at least one gas inlet line, for delivering the analyte gas from a supply of analyte gas to the separation device;
at least one detector, for detecting components of the analyte gas;
at least one gas outlet line, for delivering the components from the separation device to the detector;
a first split line in fluid communication with the gas inlet line at a first junction, and a first split valve for controlling gas flow in the first split line;
wherein opening of the first split line releases a part of a gas flow through the first split line and thereby reduces a flow rate through the separation device.

2. The system of claim 1, further comprising a second split line in fluid communication with the gas outlet line at a second junction, upstream from the detector, and a second split valve for controlling gas flow in the second split line.

3. The system of claim 2, wherein the second split valve for controlling gas flow is arranged at the second junction, the valve having a first position in which gas is able to flow through the second split line and the gas outlet line towards the detector, and a second position in which gas is able to flow along the gas outlet line towards the detector but is prevented from flowing along the second split line.

4. The system of claim 2, wherein the first split line and the second split line meet at a split line junction, and wherein a flow control gas line is connected to the split line junction.

5. The system of claim 4, wherein the split line junction comprises a split line valve for selectively controlling gas flow in the first split line, the second split line and/or the flow control gas line.

6. The system of claim 4, wherein the flow control gas line further comprises a flow controlling device that is provided as a first restriction line and a second restriction line that meet at a restriction junction that is fluidly connected to the flow control gas line, and wherein the first restriction line and the second restriction line each comprise a fixed flow restriction for controlling gas flow.

7. The system of claim 6, wherein a valve for controlling gas flow is positioned at the restriction junction, the valve having a first position, in which gas is able to flow through the first restriction line but is prevented from flowing through the second restriction line, and a second position, in which gas is able to flow through the second restriction line but is prevented from flowing through the first restriction line.

8. The system of claim 1, wherein the first and/or second split valve has a first position in which gas is able to flow through the split line, and a second position in which gas is prevented from flowing through the split line.

9. The system of claim 1, wherein the first split line and/or the second split line is open to atmosphere.

10. The system of claim 1, wherein the first split line and/or the second split line is connected to a gas supply line for providing gas into the supply of analyte gas and/or a sample introduction system for providing a sample into the supply of analyte gas.

11. The system of claim 1, wherein the first split valve for controlling gas flow is arranged at the first junction, the valve having a first position in which gas is able to flow through the first split line and the gas inlet line towards the separating device, and a second position in which gas is able to flow along the gas inlet line towards the separation device but is prevented from flowing through the first split line.

12. The system of claim 1, wherein the analyte gas is provided in a carrier gas that is preferably selected from helium and argon.

13. The system of claim 1, where the supply of analyte gas is provided by a chemical reactor.

14. The system of claim 1, further comprising a chemical trap that is arranged upstream of the separation device on the gas inlet line.

15. The system of claim 1, further comprising a secondary carrier gas inlet line that is fluidly connected to the gas inlet line at a carrier gas junction, between the analyte gas supply and the first split line.

16. The system of claim 15, wherein the secondary carrier gas inlet line is provided with gas flow control means for controlling gas flow into the gas inlet line.

17. The system of claim 15, further comprising an analyte gas split line that is arranged on the gas inlet line, between the analyte gas supply and the carrier gas junction, the analyte gas split line further comprising a valve for directing flow of gas through the analyte gas split line, the valve having a first position in which analyte gas is able to flow through the analyte gas split line and in which gas is prevented from flowing through the gas inlet line downstream from the analyte gas split line, and a second position in which analyte gas is prevented from flowing through the analyte gas split line but is able to flow through the gas inlet line.

18. The system of claim 15, further comprising a valve arranged at, or in fluid communication with, the carrier gas junction, wherein the valve has a first position in which gas is able to flow from the analyte gas supply through the gas inlet line towards the first junction and in which the secondary carrier gas is prevented from flowing into the gas inlet line, and a second position in which analyte gas is prevented from flowing from the analyte gas supply through the gas inlet line towards the first junction and in which the secondary carrier gas is able to flow into the gas inlet line, towards the first junction.

19. The system of claim 1, further comprising a second separation device, wherein the second separation device is arranged downstream from the second split line, between the second split line and the detector.

20. The system of claim 1, further comprising a controller for controlling valve position of at least one of the valves, and wherein the controller optionally receives an input from the detector, and wherein the position of at least one valve is based on the determination of presence or absence of at least one component of the analyte gas.

21. The system of claim 20, wherein the controller receives an input from the detector about at least one analyte gas, and wherein the position of at least one valve is adjusted based on a determination of the concentration of the analyte gas.

22. The system of claim 20, wherein the controller is configured to simultaneously adjust the position of two or more valves, so that the controller is configured to adjust the position of the first split valve and the second split valve, so that when the first split valve is open the second split valve is closed, and so that when the first split valve is closed the second split valve is open.

23. The system of claim 1, wherein the separation device is a gas chromatograph.

24. A method of concentrating a sample gas for detection in a continuous flow retention-based analytical device having a gas inlet and a gas outlet, the method comprising steps of:
    providing a flow of gas into the analytical device at a first flow rate, wherein the gas contains an analyte gas comprising at least one component that is retained in the device and a carrier gas that is not retained;
    reducing the flow rate of the carrier gas into the analytical device to a second flow rate prior to at least one selected component of the analyte gas emerging at the gas outlet of the analytical device, by splitting away a part of the gas stream through a first split line on, or in fluid communication with, an inlet gas line that is connected to the gas inlet, wherein the second flow rate is lower than the first flow rate;
    whereby the at least one selected component of the analyte gas is concentrated in the carrier gas as it travels through the retention-based analytical device at the second flow rate.

25. The method of claim 24, wherein the analytical device is a separation device.

26. The method of claim 24, wherein the first flow rate is in the range of 40 to 400 mL/min, and wherein the second flow rate is in the range of 10 to 100 mL/min.

27. The method of claim 24, wherein the reducing of flow rate of the carrier gas to the second flow rate is performed simultaneously with, or immediately following, the replacing of the mixture of analyte gas and carrier gas with carrier gas.

28. The method of claim 24, wherein the emerging of analyte gas at the outlet of the separation device is monitored by an analyte gas detector that is located within, or downstream from, the separation device.

29. The method of claim 28, wherein gas flow rate into the analyte gas detector is maintained so as to be substantially equal to the second flow rate when the gas enters the analytical device at the first flow rate, by splitting away excess gas flow through a second split line on, or in fluid communication with, an outlet gas line between the outlet of the analytical device and the detector, said second split line being closed when the gas enters into the analytical device at the second flowrate.

30. The method of claim 24, further comprising providing a first split line for the flow of gas upstream of the gas inlet and providing a second split line downstream of the outlet for the analyte and carrier gas; and further comprising having the first split line closed and the second split line open while the gas flows into the device at the first flow rate and having first split line open and the second split line closed while the carrier gas flows into the device at the second flow rate.

31. The method of claim 24, wherein the analyte gas comprises a plurality of components that are temporarily retained in the device; the method further comprising reducing the flow rate of the carrier gas into the analytical device to the second flow rate prior to at least one selected component of the analyte gas emerging at the gas outlet of the analytical device; whereby the at least one selected component of the analyte gas is concentrated in the carrier gas as it travels through the retention-based analytical device at the second flow rate.

32. The method of claim 31, further comprising reducing the flow rate of the carrier gas into the analytical device to the second flow rate after at least one non-selected component of the analyte gas has emerged at the gas outlet of the analytical device.

* * * * *